(12) United States Patent
Mager et al.

(10) Patent No.: US 7,018,328 B2
(45) Date of Patent: Mar. 28, 2006

(54) TISSUE STABILIZER

(75) Inventors: Larry F. Mager, Pleasanton, CA (US); Jerome B. Riebman, Sunnyvale, CA (US); Raymond Bertolero, Danville, CA (US); Arthur A Bertolero, Danville, CA (US); Tamer Ibrahim, Oakland, CA (US)

(73) Assignee: Endoscopic Technologies, Inc., Danville, CA (US)

(*) Notice: Subject to any disclaimer, the term of this patent is extended or adjusted under 35 U.S.C. 154(b) by 600 days.

(21) Appl. No.: 10/297,791

(22) PCT Filed: Feb. 9, 2001

(86) PCT No.: PCT/US01/04263

§ 371 (c)(1),
(2), (4) Date: Dec. 9, 2002

(87) PCT Pub. No.: WO01/58362

PCT Pub. Date: Aug. 16, 2001

(65) Prior Publication Data

US 2004/0015047 A1    Jan. 22, 2004

Related U.S. Application Data

(60) Provisional application No. 60/182,048, filed on Feb. 11, 2000.

(51) Int. Cl.
*A61F 2/00* (2006.01)

(52) U.S. Cl. .................. 600/37; 606/206; 606/235
(58) Field of Classification Search ............... 600/37, 600/201–210, 217–235; 606/191, 194
See application file for complete search history.

(56) References Cited

U.S. PATENT DOCUMENTS

| 5,885,271 | A  | * | 3/1999  | Hamilton et al. | ............... 606/1   |
| 6,007,486 | A  | * | 12/1999 | Hunt et al.     | ................. 600/205 |
| 6,338,738 | B1 | * | 1/2002  | Bellotti et al. | .............. 606/232 |
| 6,511,416 | B1 | * | 1/2003  | Green et al.    | .................. 600/37 |

FOREIGN PATENT DOCUMENTS

| EP | 0791329 | * | 8/1997 |
| EP | 0791330 | * | 8/1997 |
| WO | 9837814 | * | 9/1998 |

* cited by examiner

*Primary Examiner*—John P. Lacyk
(74) *Attorney, Agent, or Firm*—Gregory Scott Smith; Carol D. Titus; GSS Law Group

(57) ABSTRACT

A tissue stabilizer is disclosed that comprises a malleable planer foot integrated into a flexible membrane and is useful for stabilizing tissue such as the heart while performing surgery thereon. The malleable planar foot has an open central region and a rigid arm connected to the foot. The membrane integrated with the foot has a shape approximating the foot, a lower section having a bottom surface for contacting the tissue to be stabilized, and an upper section opposite the lower section. The membrane has an inner chamber in fluid communication through an opening with a plurality of suction ports on the bottom surface. An outlet port connects the inner chamber and suction ports to a negative pressure source. The tissue stabilizer has a centrally-located open region through which the tissue to be stabilized can be accessed and is designed so that when the bottom surface of the membrane is positioned on a tissue to be stabilized and a negative pressure is applied to the outlet port, the bottom surface tends to conform to the surface contour of the tissue to be stabilized through the action of suction by the ports and compression by the foot.

42 Claims, 12 Drawing Sheets

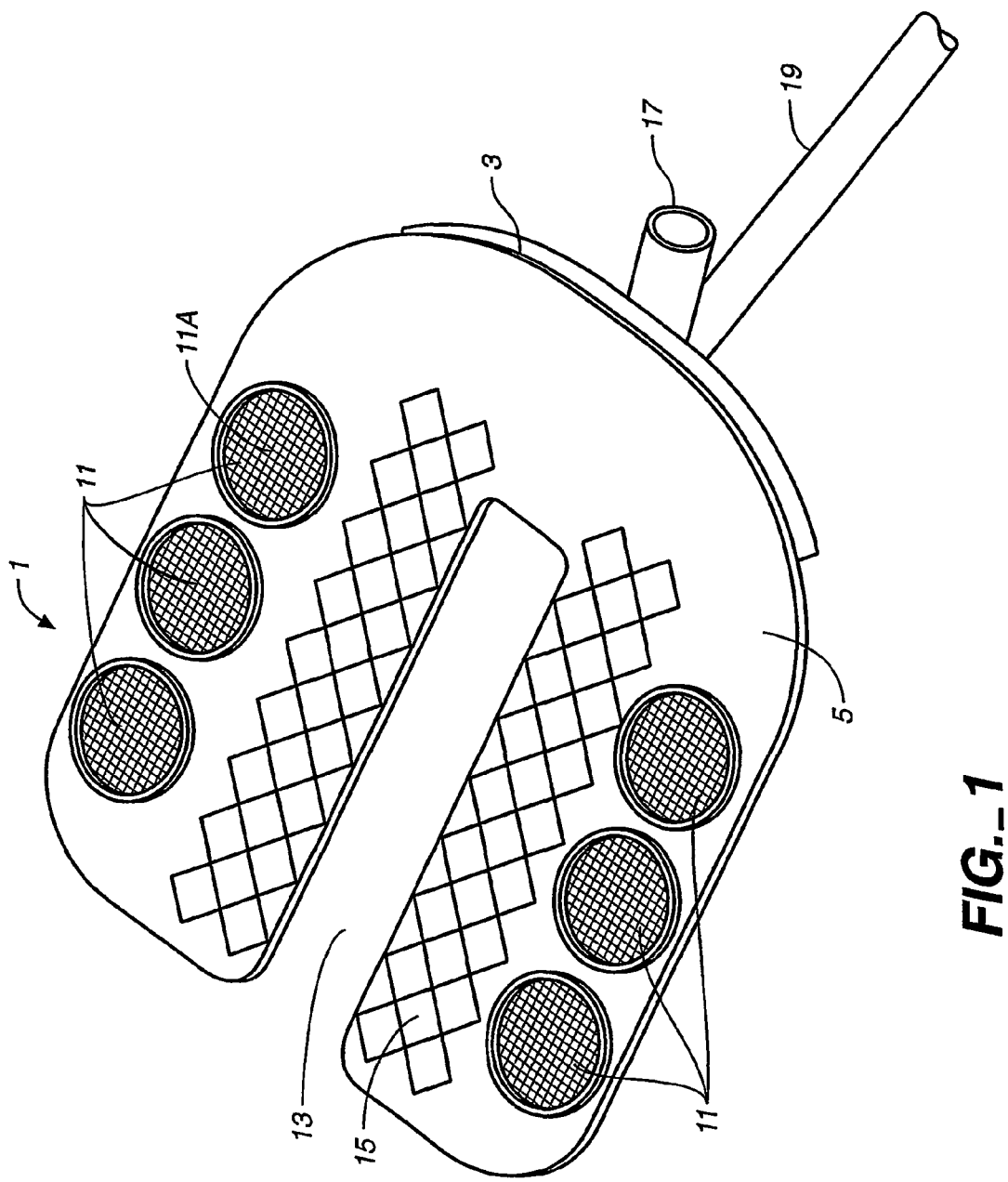
FIG._1

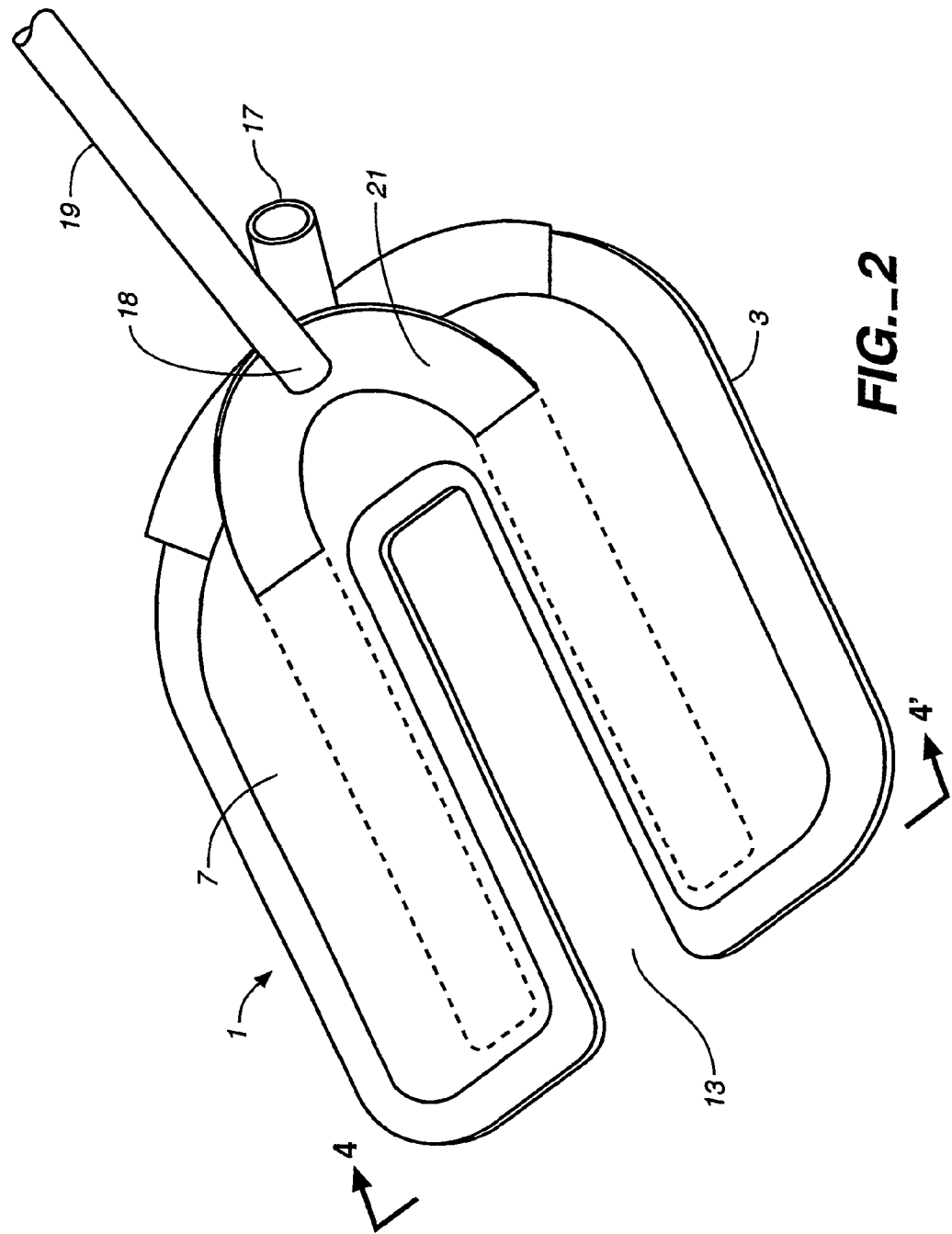

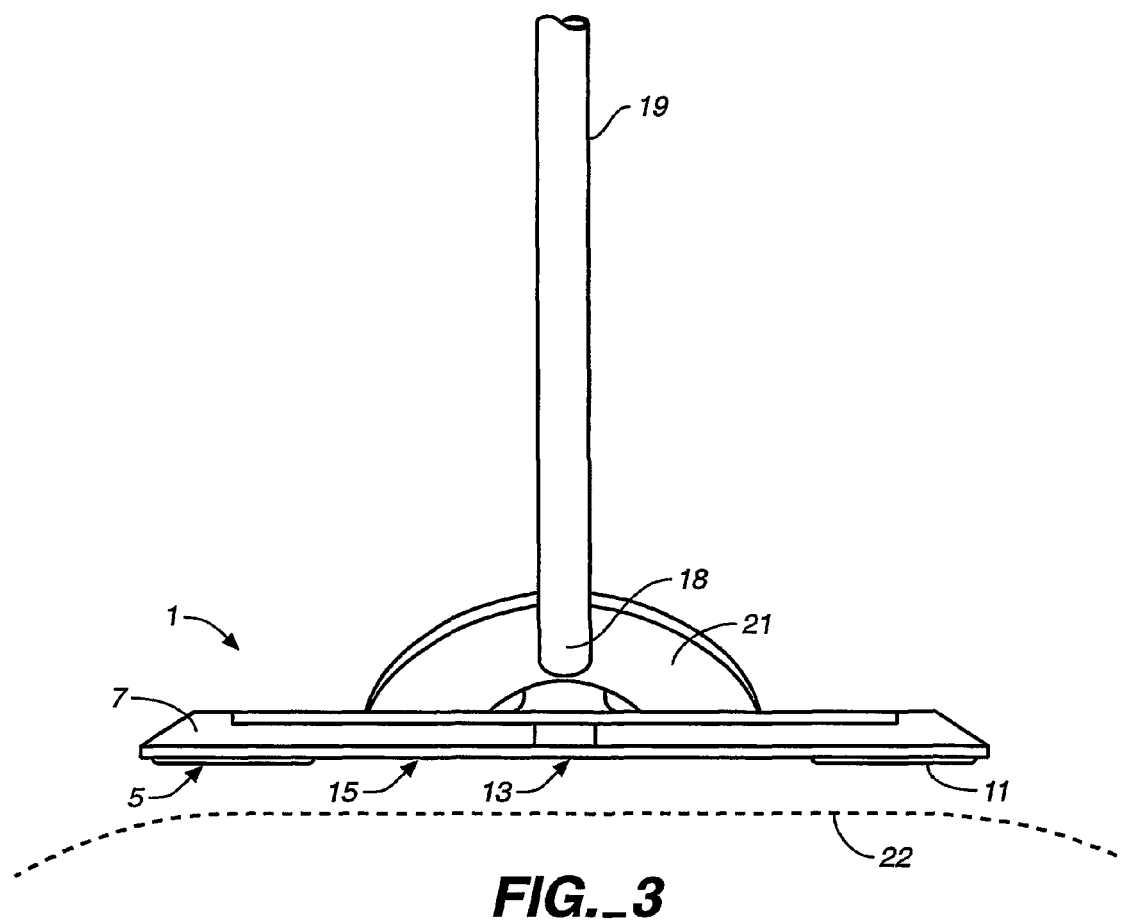
FIG._3

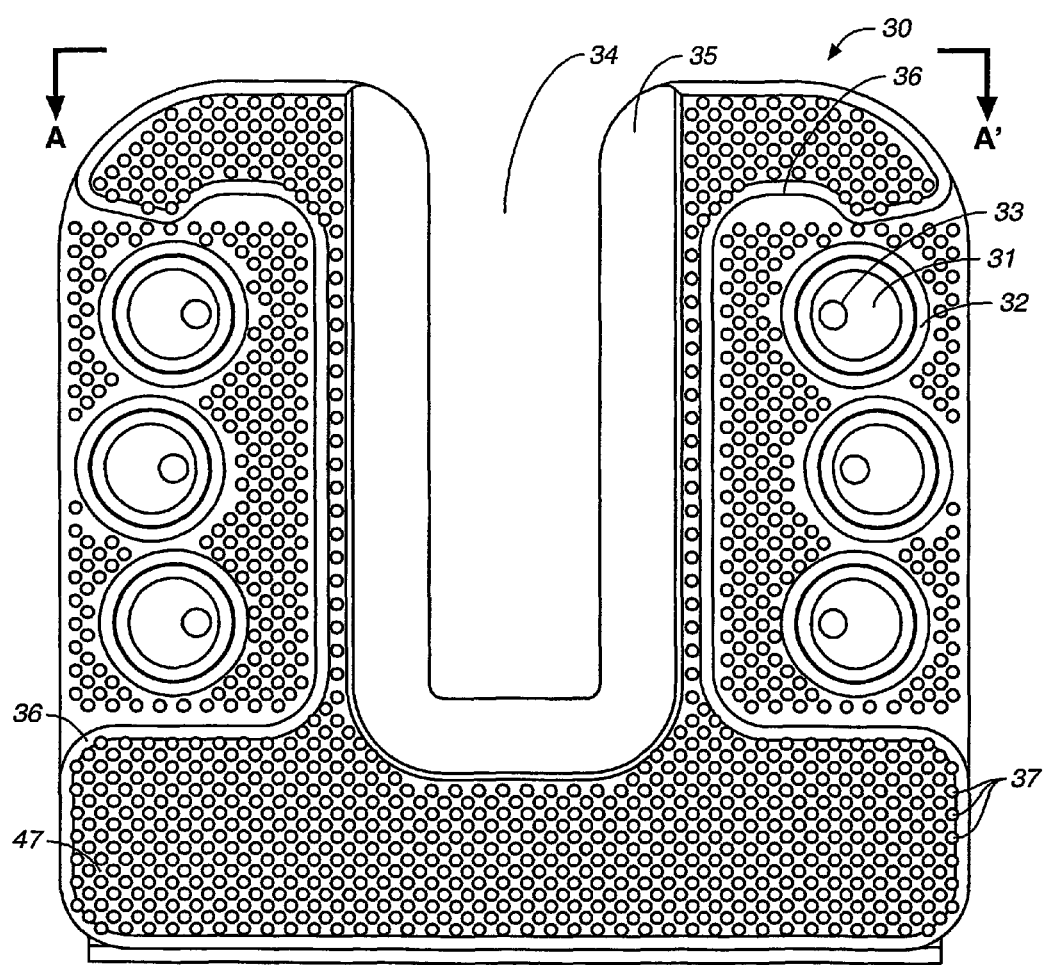
FIG._4

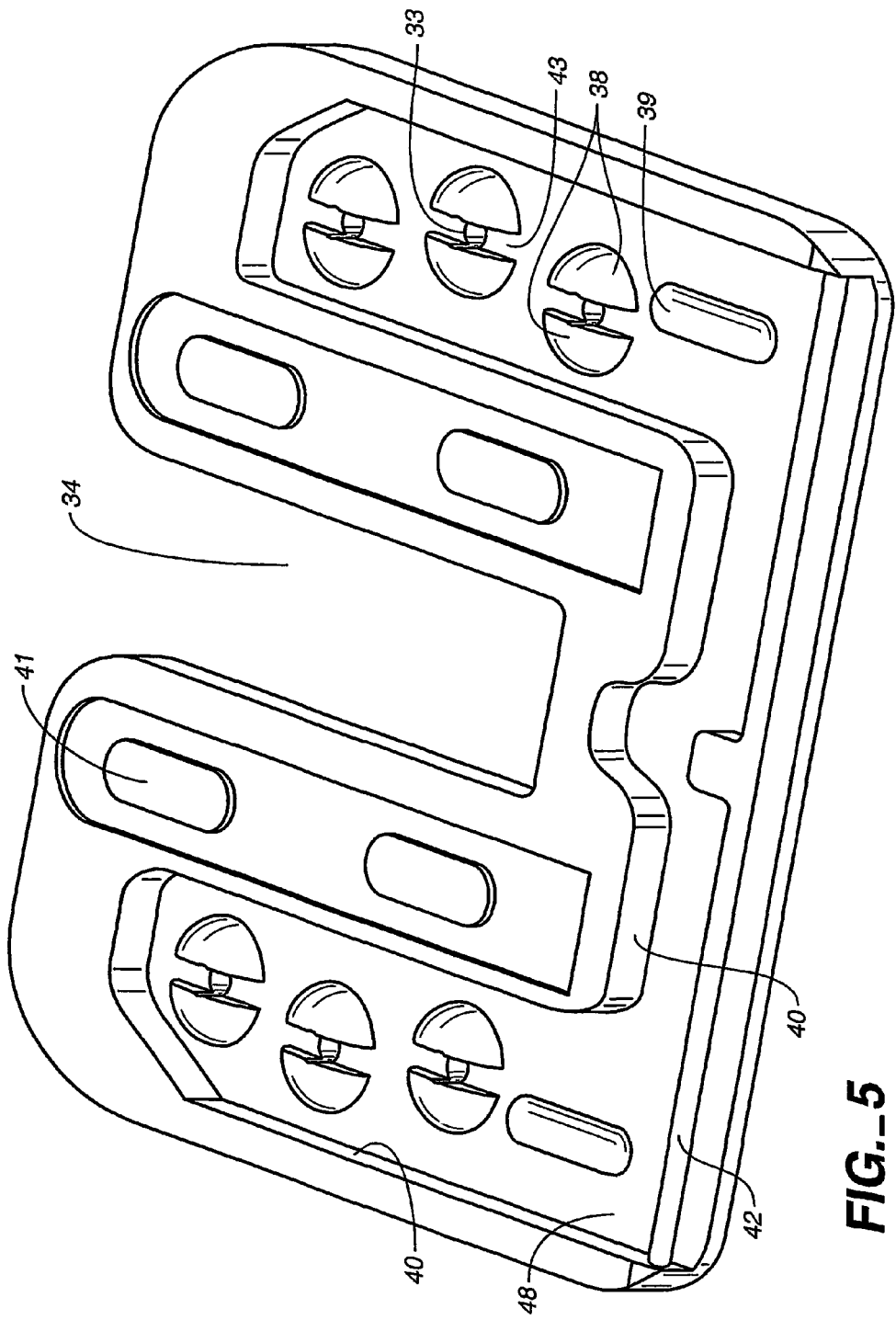
FIG._5

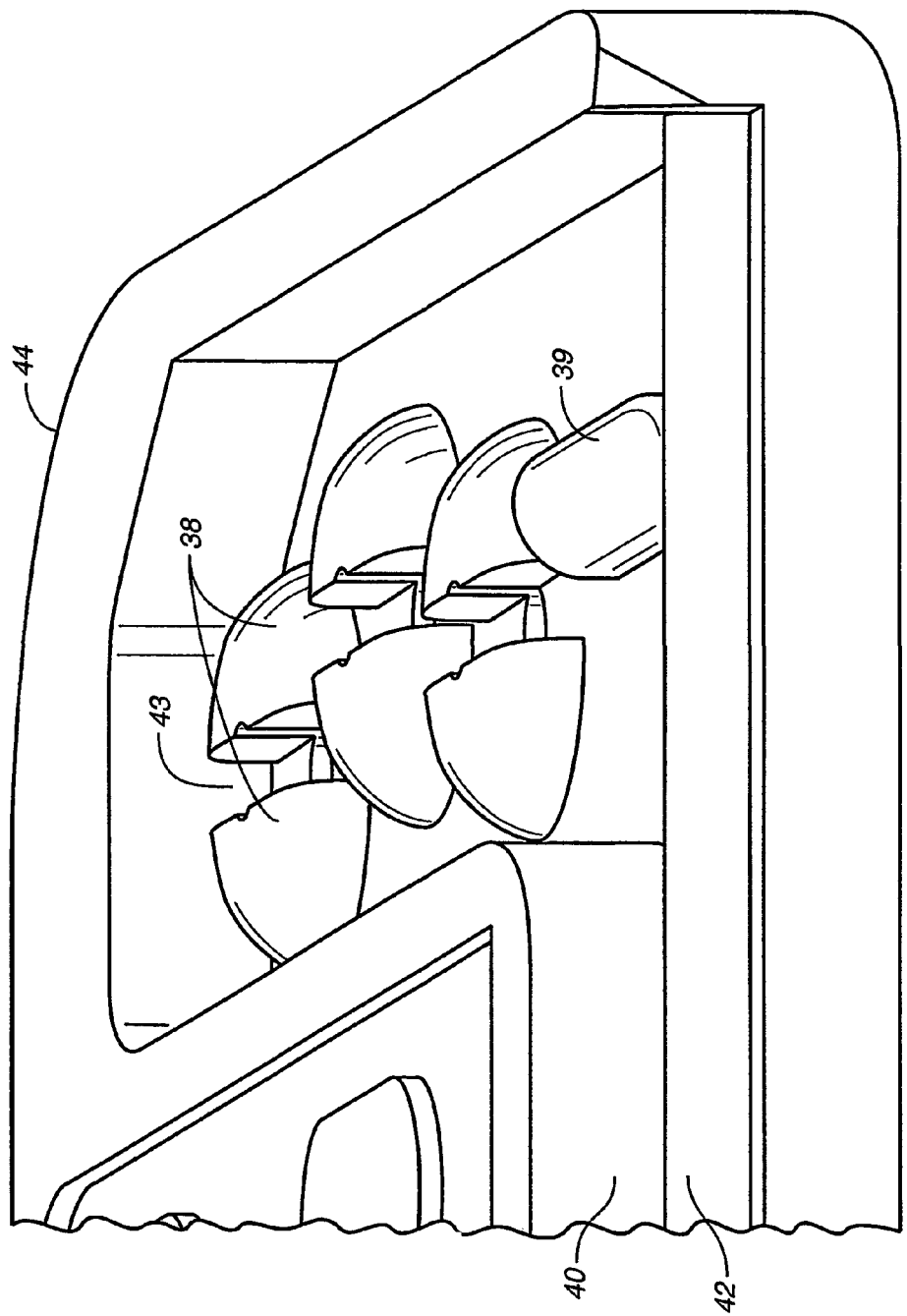
FIG._6

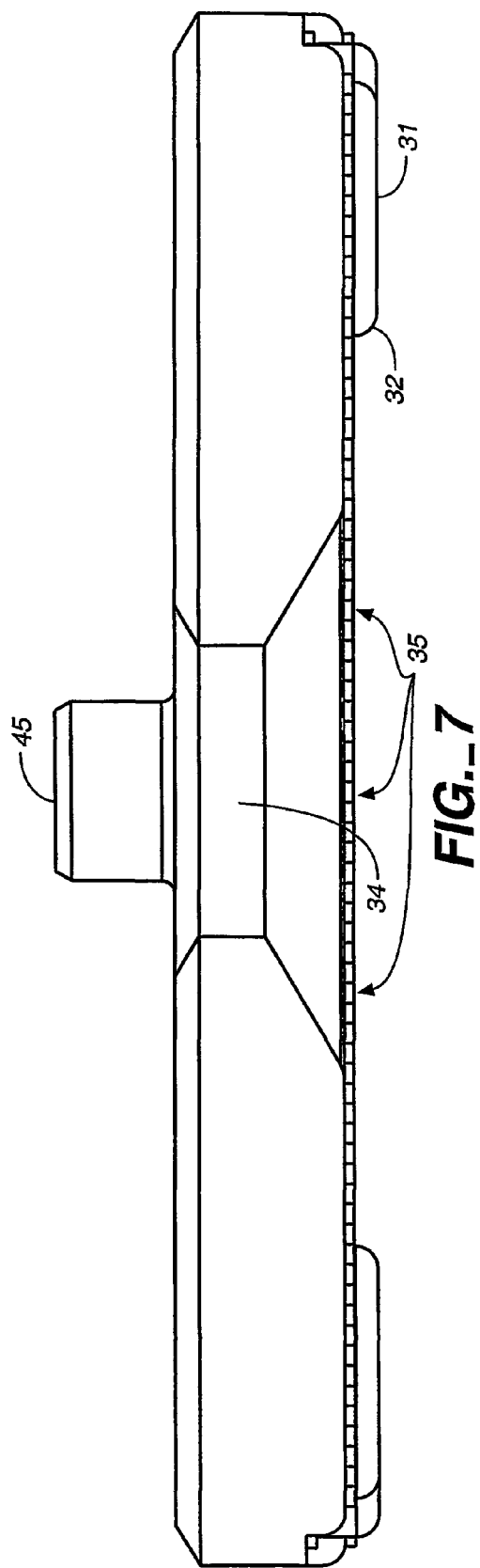

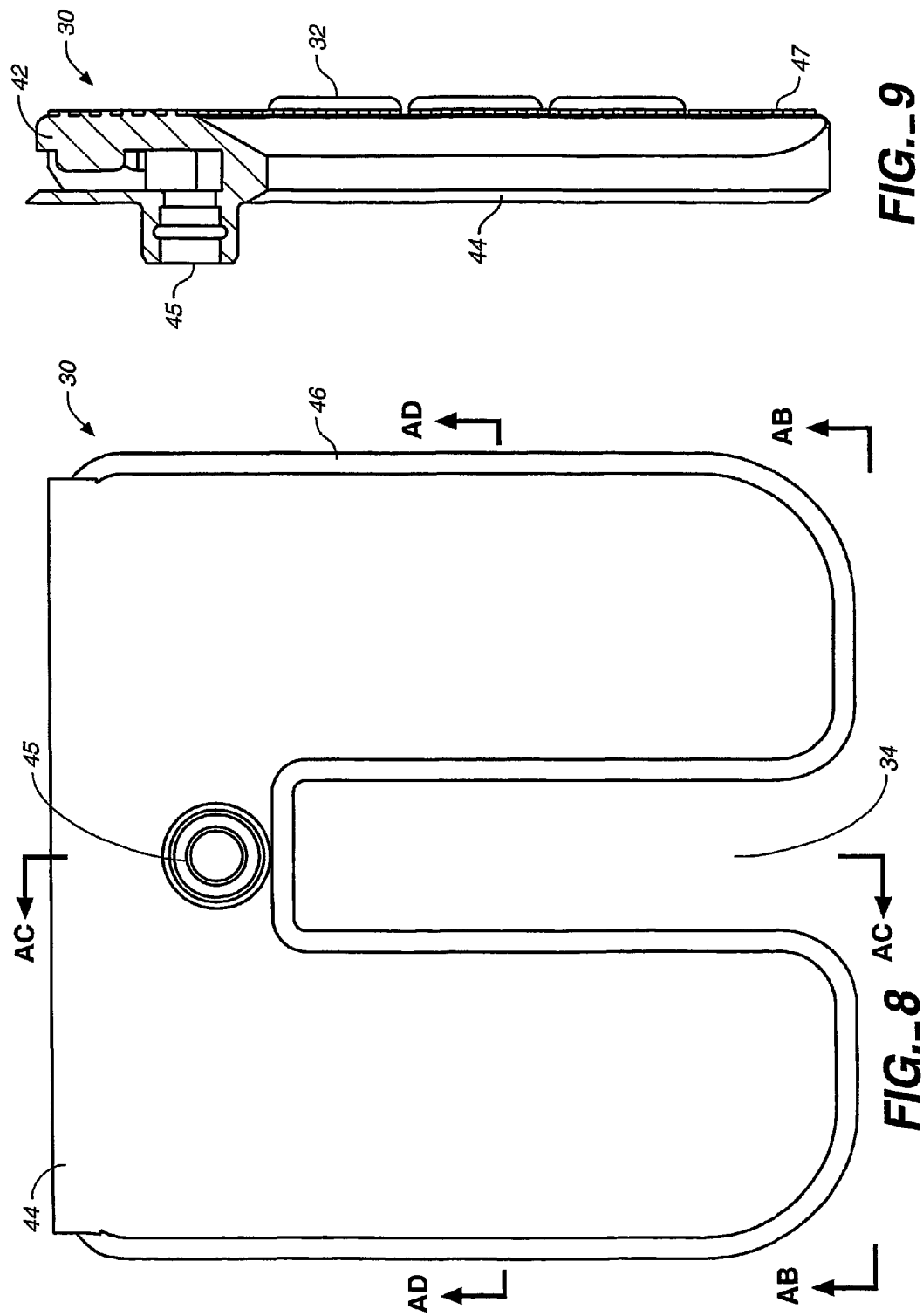

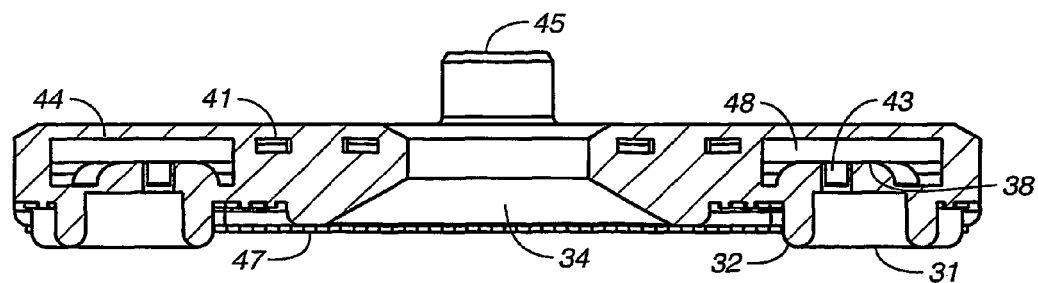
FIG._10
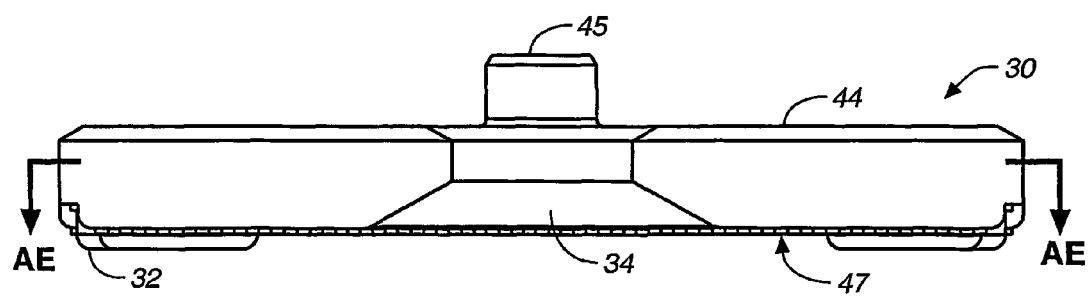
FIG._11

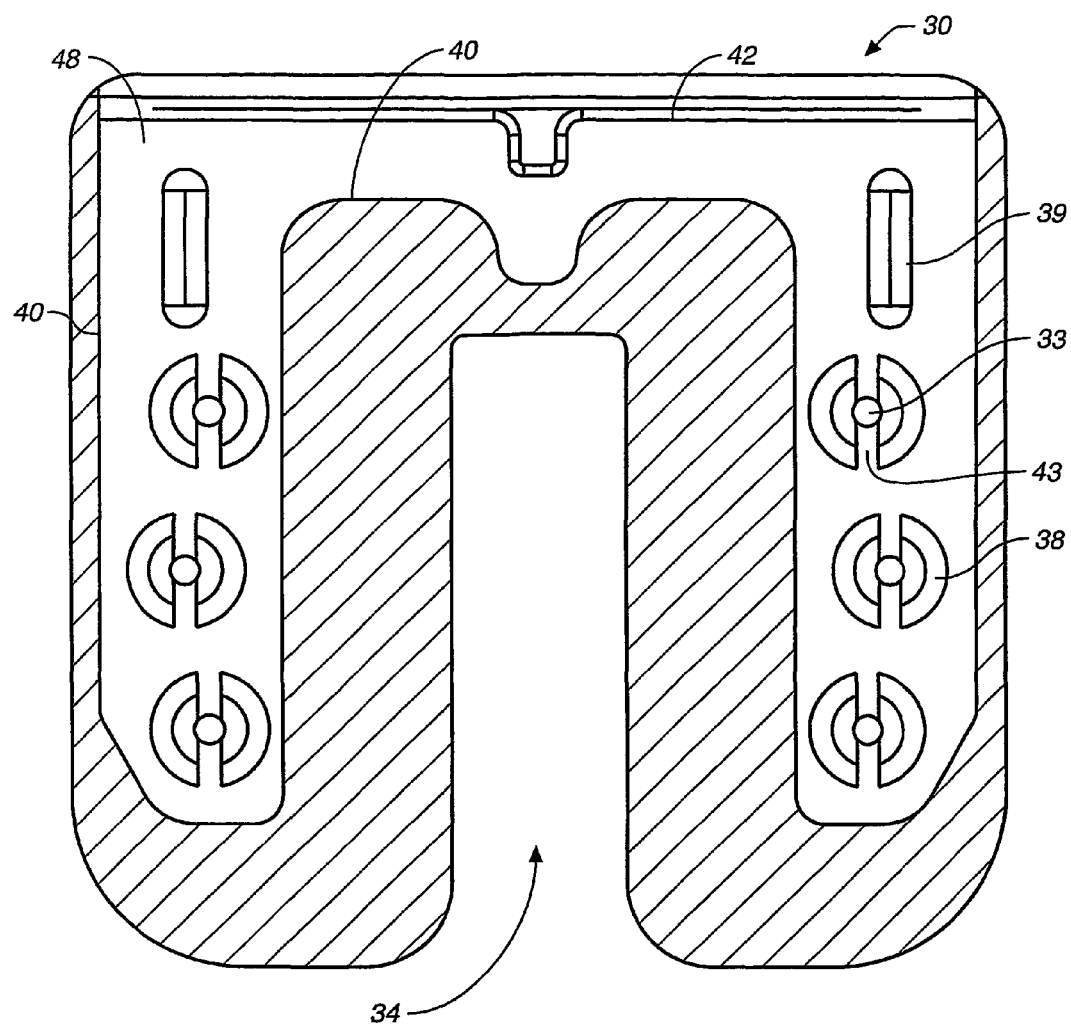
FIG._12

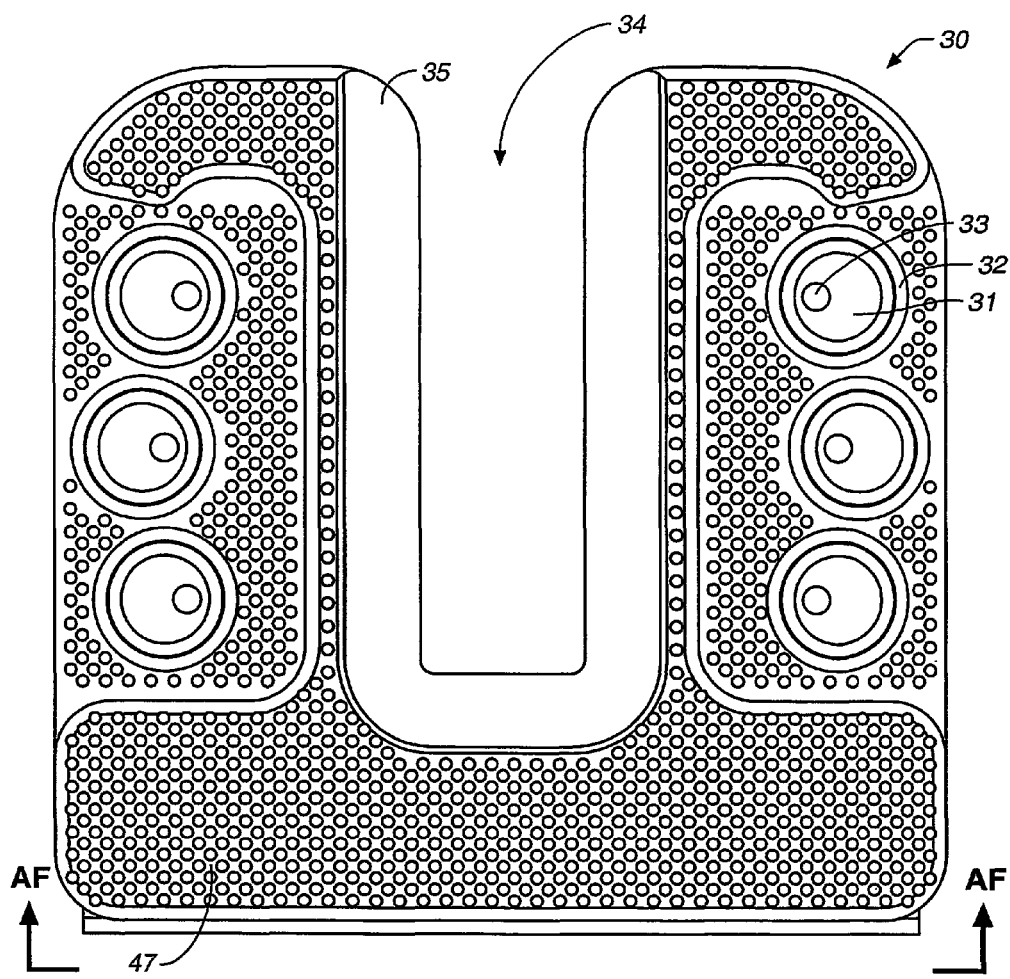
*FIG._13*
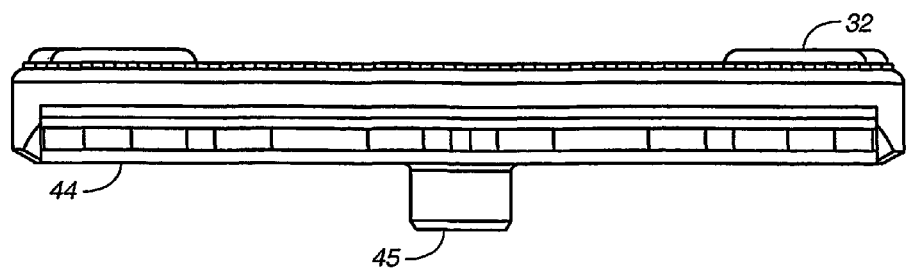
*FIG._14*

TISSUE STABILIZER

CROSS REFERENCE

This patent application claims priority to U.S. provisional patent application 60/182,048, filed Feb. 11, 2000 and is a continuation in-part thereof.

FIELD OF THE INVENTION

This invention relates to a surgery assistance device that stabilizes tissue to be operated on by a combination of suction and compression.

BACKGROUND

When surgeons perform a surgical procedure on a tissue it is often important to stabilize the tissue so that the area that is being operated on is stable to ensure the accuracy of the surgeon's work. This is particularly important when operating on an internal organ such as the heart, whether a beating heart or a stopped heart. The tissue needs to be stabilized in a manner that exposes the area being operated on to the surgeon and needs to be easily used by the assistant whether such a person is another doctor or a nurse. The device of this invention is designed to give improved stabilization especially to a beating heart with motion reduction of the tissue in the X, Y, and Z directions.

SUMMARY OF THE INVENTION

One aspect of this invention is a tissue stabilizer that comprises a malleable planar foot integrated into a flexible membrane. The malleable planar foot has an open central region and a rigid arm connected to the foot. The membrane integrated with the foot has a shape approximating the foot, a lower section having a bottom surface for contacting the tissue to be stabilized, and an upper section opposite the lower section. The membrane has an inner chamber in fluid communication through an opening with a plurality of suction ports on the bottom surface. An outlet port connects the inner chamber and suction ports to a negative pressure source. The tissue stabilizer has a centrally-located open region through which the tissue to be stabilized can be accessed and is designed so that when the bottom surface of the membrane is positioned on a tissue to be stabilized and a negative pressure is applied to the outlet port, the bottom surface tends to conform to the surface contour of the tissue to be stabilized through the action of suction by the ports and compression by the foot. A surgeon is then able to operate on the tissue through the open region.

Another aspect of this invention is a tissue stabilizer that comprises a flexible membrane suitable for integration with a malleable planar foot having a central access opening. The membrane comprises a lower section having a bottom surface for contacting the tissue to be stabilized and a top section opposite the lower section. Together the sections form an inner chamber in the membrane. A plurality of suction ports are located on the bottom surface, each suction port being in fluid communication with the chamber through an opening. An outlet port is in fluid communication with the inner chamber and suction ports and can be connected to a negative pressure source. The membrane has a centrally-located open region through which the tissue to be stabilized can be accessed and a sleeve between the top and bottom sections designed to receive the malleable planar foot, which foot has an extension on each side of the central region. When the planar foot is inserted into the sleeve, the membrane and foot may be positioned on a tissue to be stabilized, and a negative pressure is applied to the outlet port. The bottom surface conforms to the surface contour of the tissue to be stabilized through the action of the suction ports and compression by the foot.

Still another aspect of the invention is a method for stabilizing tissue. The method comprises positioning the tissue stabilizer of this invention on the tissue to be stabilized, then attaching a negative pressure source to the outlet port and providing compressive force to the foot though the rigid arm for a time sufficient to conform the proximal surface of the tissue stabilizer to the tissue area. After the tissue stabilizer has been placed upon the tissue, an operation may be performed on the tissue through the central open region of the foot and membrane. The stabilizer comprises a malleable, planar foot having a central opening, a rigid arm connected to the foot, and a membrane integrated with the foot. The membrane has a shape approximating the foot, a lower section having a bottom surface for contacting the tissue to be stabilized, and a top section opposite the bottom section. An inner chamber in the membrane is in fluid communication with a plurality of suction ports on the bottom surface and with an outlet port for connecting to a negative pressure source. The stabilizer has a centrally-located open region through which the tissue to be stabilized can be accessed and the stabilizer is designed so that when the bottom surface of the membrane is positioned on a tissue to be stabilized and a negative pressure is applied to the outlet port, the bottom surface conforms to the surface contour of the tissue to be stabilized through the action of suction and compression.

A further aspect of the invention is a process for making the tissue stabilizer of this invention using an injection molding technique. An appropriate mold is prepared and provided with removable mandrels for the inner chamber and the outlet port of the membrane. The foot and connecting rod are positioned with the mold to be integrated into the membrane. A polymeric material is injected into the mold and cured. The mandrels are removed and the upper section and lower section adhered to form the chamber.

Other aspects of the invention will be apparent to one of skill in the art upon reading the following specification and claims. Details of the invention are discussed hereinafter.

BRIEF DESCRIPTION OF THE DRAWINGS

FIG. 1 is a perspective view of a representative device of this invention showing the bottom side of the device.

FIG. 2 is a top view of the topside of a representative device of this invention.

FIG. 3 is a front view of a representative device shown in FIG. 2 along line 4–4'.

FIG. 4 is a bottom view of a representative device of this invention.

FIG. 5 is a side perspective view of the internal chamber of a representative device of this invention.

FIG. 6 is a close-up side perspective view of the right-hand region of the internal chamber depicted in FIG. 5.

FIG. 7 is an end view of a representative device of this invention taken along line A–A' of FIG. 4.

FIG. 8 is a top view of a representative device of this invention.

FIG. 9 is a cross-sectional view taken along lines AC—AC in FIG. 8.

FIG. 10 is a cross-sectional view taken along lines AD—AD of FIG. 8.

FIG. 11 is an end view taken along lines AB—AB in FIG. 8.

FIG. 12 is a cross-sectional downward view of a representative example of a device of this invention along lines AE—AE in FIG. 11.

FIG. 13 is a bottom view of a representative device of this invention and shows the surface opposite that shown in FIG. 8.

FIG. 14 is a rear view of a representative device of this invention shown in FIG. 13 taken along line AF—AF.

DETAILED DESCRIPTION OF SPECIFIC EMBODIMENTS

Overview

Figure 15:
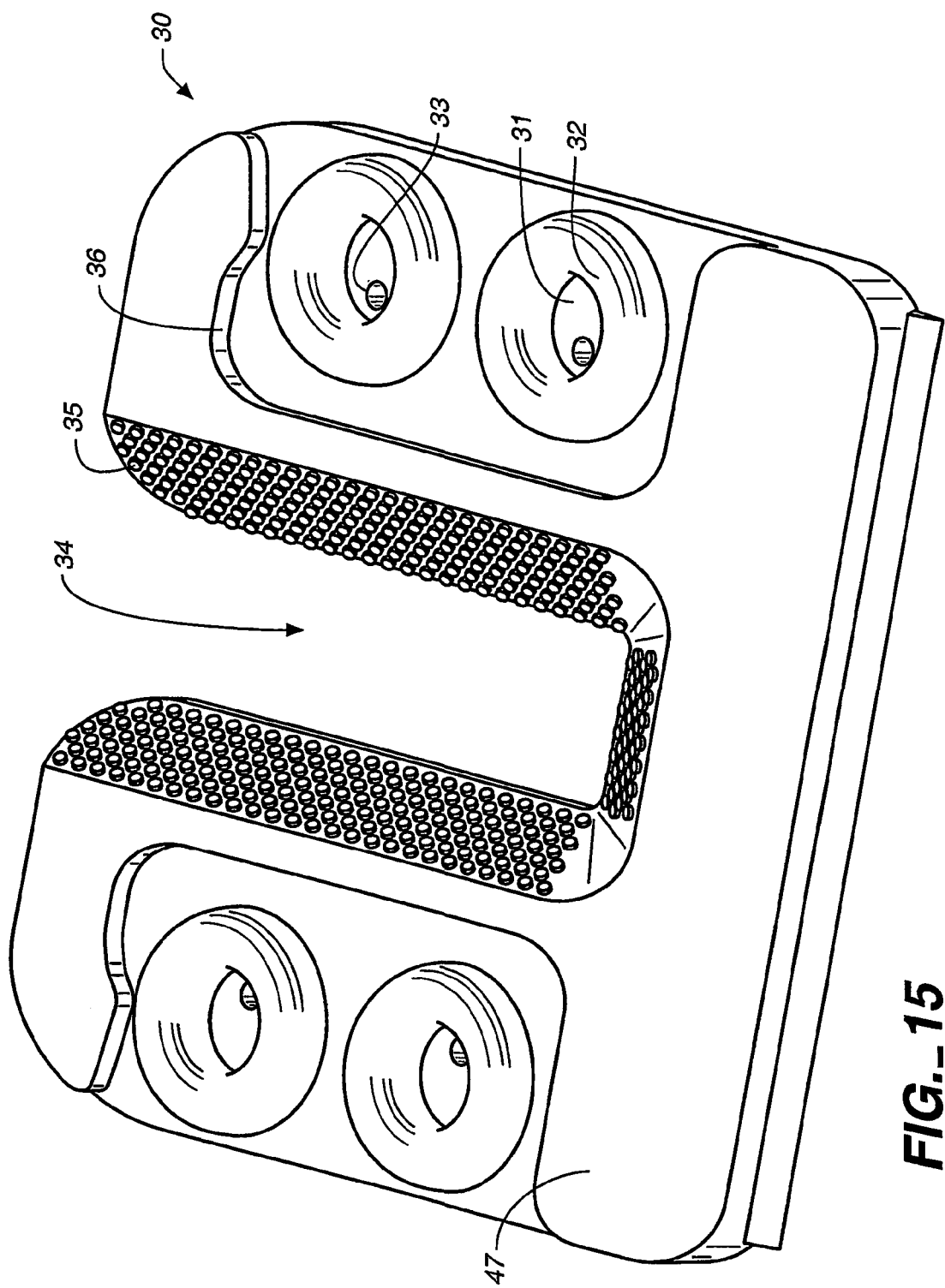
FIG. 15 is a three-dimensional perspective of the bottom side of a device of this invention wherein there are a total of four suction ports on the bottom of the device.

The device of this invention readily is used in open-heart surgery and in surgery on other tissues and organs. The tissue stabilizer is a combination of compression and suction forces that are applied to the tissue, particularly a beating heart, in the stabilization process. In functioning to stabilize the tissue of a beating heart, for example, during anastomosis, the forces transmitted from the beating heart pass through the separate zones of suction and compression thus damping those forces and minimizing the motion at the anastomotic site. The amount of compression force required to stabilize the epicardial tissue at the anastomotic site is reduced, thus minimizing trauma, without introducing additional trauma due to the addition of suction. The adherence of the device to the epicardial tissue aids preventing movement, or drift, away from the anastomotic site.

Characteristics of the Device of this Invention

One aspect of this invention is a tissue stabilizer that comprises a malleable planar foot integrated into a flexible membrane. The malleable planar foot has an open central region and a rigid arm connected to the foot. The membrane integrated with the foot has a shape approximating the foot, a lower section having a bottom surface for contacting the tissue to be stabilized, and an upper section opposite the lower section. The membrane has an inner chamber in fluid communication through an opening with a plurality of suction ports on the bottom surface. An outlet port communicates with the inner chamber and suction ports and is connectable to a negative pressure source. The tissue stabilizer has a centrally-located open region through which the tissue to be stabilized can be accessed and is designed so that when the bottom surface of the membrane is positioned on a tissue to be stabilized and a negative pressure is applied to the outlet port, the bottom surface tends to conform to the surface contour of the tissue to be stabilized through the action of suction by the ports and compression by the foot. A surgeon is then able to operate on the tissue through the open region.

Turning now to FIG. 1, one can see a representative tissue stabilizer shown in perspective as 1. The stabilizer has a membrane shown as 3 with an inner chamber (not shown) in the interior of the device formed by the upper and lower sections of the device. The stabilizer has a bottom surface 5 of the lower section and a top surface 7 of the upper section (not shown in FIG. 1). The bottom surface is the surface that contacts the tissue to be stabilized. The inner chamber is not shown in FIG. 1 because the view is an exterior view. On the bottom surface of the stabilizer one sees a plurality of suction ports 11 around the perimeter. While FIG. 1 shows a total of 6 suction ports, the number may vary between 2 and 10, preferably there are 4 or 6 ports, equally distributed as shown. Each port is in fluid communication with the inner chamber that leads to an outlet port 17. The suction ports may be covered by a mesh or screen as shown as 11A and are preferably shaped like the suction ports of an octopus, i.e. they are circular, although other shapes such as squares, ovals, etc. may be employed. The outlet port 17, which is in fluid communication with the inner chamber and the suction ports, is designed to be connected to a negative pressure source. Thus, a vacuum is applied to draw air out of the inner bladder and create suction along the suction ports.

The bottom surface shown also has at least a portion (shown as an area 15) that has been modified to aid in maintaining bottom surface against the tissue being stabilized and preventing slippage of the stabilizer, i.e. the modification is such that the movement relative to the tissue surface is reduced. The modification may be done by texturing the surface with cross-hatching as shown in FIG. 1, providing rows of dimples or bumps, or other designs that reduce movement relative to the tissue surface, e.g. stippling. Alternatively, the surface may be modified by placing a physiologically-acceptable adhesive on it to assist in adhering the lower surface to the tissue to be stabilized. While the arrangement shown in FIG. 1 shows the modified area immediately around the central opening 13 with the suction ports around the perimeter of the lower surface, the ports may be located around the central opening directly under the planar foot with the modified area (as indicated by the cross-hatching) located around the perimeter. It is preferred, however, that the malleable planar foot be positioned so that the bottom planar surface of the foot does not press down on the suction ports. While FIG. 1 shows only a portion of the bottom surface modified, nearly the entire bottom surface can be modified. Preferably, the bottom surface of the suction ports are not textured, as this could adversely affect the suction against the tissue.

If the bottom surface is modified using a physiologically acceptable adhesive, various adhesive approaches may be used. The adhesive maybe applied to the tissue and the bottom surface placed on the tissue, e.g. a heart. Alternatively, and preferably, the adhesive is applied to the bottom surface prior to the application of the device to the tissue to be stabilized. The adhesive must be sufficiently biocompatable to dissipate relatively harmlessly in the body fluids or be removable with minimal difficulty. Water soluble biocompatable adhesive are known and used in various surgical and medical procedures. Hydrogel polymers of hydroxy ethylcelulose or hydroxy melthocelulose and hydrogel copolymers of these two are examples. Polymers with acrylic acid and acrylic esters are also known to be useful biocompatible adhesives. Polyvinyl alcohol is another water-soluble adhesive that may be used. If the device has a bottom surface that is made of a silicon rubber, a biocompatable silicon rubber having a durometer rating of approximately zero (which means that it is nearly a liquid) is useful in the invention.

The connector arm 19 is connected to the inner malleable foot 21, which is not shown in FIG. 1. The inner malleable foot is designed to provide compression, which acts in conjunction with and adjacent to the suction ports on the bottom surface, to maintain contact with the surface of the tissue. Thus, the device in operation is placed on the tissue to be stabilized, for example a beating heart, and the stabilization of the tissue adjacent to the tissue targeted for stabilization occurs through compression while the stabilization of the tissue adjacent to the tissue under compression is stabilized via suction provided by ports 11. This creates varying zones of stabilization proximal to the target tissue by gradually isolating the movements or forces transmitted from unstabilized tissue. Portions of the tissue are drawn into the ports due to the vacuum that is drawn through out at port 17. With this combination, a surgeon can position the device to stabilize the desired tissue so that the central open region 13 is arranged to expose part of the tissue to be operated upon. While the preferred design of the planar foot shown in FIG. 1 is basically a "U" shaped design, it may be circular, rectangular, etc. design as well, so that the open region would be the central part with the malleable foot surrounding it and the suction ports located at the perimeter not directly beneath the foot.

It is also possible to provide the device as a family of products which are geometrically configured or sized and specifically optimized for the tissue or region targeted for stabilization. The malleable foot, is molded to approximately conform to the tissue surface being stabilized.

Turning now to FIG. 2, one sees a top view of the tissue stabilizer 1 of this invention having the top surface 7 of the upper section. The membrane is generally shown as 3 with the connector arm 19 connected to the inner malleable foot 21. In this particular case, only a portion of the malleable foot is shown in the exterior with a dotted line showing the extent of the malleable foot in the interior of the membrane. The foot may fit into the membrane through a sleeve, which would allow the foot to be removed from the sleeve and placed into another membrane of similar design. Alternatively, the malleable foot could be injection molded into the membrane design so that the malleable foot is not removable from the bladder. Thus, the material, which coats the foot, would permanently coat it so that it would not slip out of a sleeve.

The malleable foot is manufactured out of a ductile metal or polymeric material by either a stamping process or typical machining practice. The shape can be adjusted once associated with the membrane. The connector arm is brazed, soldered, bonded, or welded onto the malleable foot. The assembled portion above is inserted into a mold and liquid silicone is injection molded around it to form the bladder as discussed hereinafter.

The device finds particular application in beating heart surgery in animals and is particularly useful for the cardiac surgeon in his or her armamentarium for coronary revascularization in humans. The device allows a surgeon to improve the patient care and perform beating heart surgery in a controlled fashion with reproducibly good results. The connector arm 19, as mentioned before, is used to provide the compression to push down and immobilize the epicardium around the target tissue to be worked upon. Once the tissue stabilizer is gently placed down on the tissue to be stabilized, the suction then pulls up on the epicardium making the tissue around the target vessel taut. The connector arm may be held by an assistant during the operation or can be connected to a stabilizer arm that is connected to the table or some other stable part of the operating theater. For example, the connector arm 19 can be attached to the adjustable arm of the Universal Stabilizer System manufactured by Endoscopic Technologies. By utilizing this combined approach, the tissue is stabilized, with motion in the X, Y and Z directions reduced significantly. The connector arm can be pivoted at point 18 so that it has multiple plains of movement. In FIG. 2, the arrows show that it can move either right or left and is connected to the malleable foot by a connecting pin. Alternatively, it could be connected through a universal joint that could be tightened to keep it in place. This device is of various sizes and can be used multi-vessel target access easily. It allows for easy surgeon and assistant flexibility and is easily used by nurses in assisting in the operation.

Turning now to FIG. 3, one sees an end view of the tissue stabilizer of this invention viewed along line 4–4' in FIG. 2. Here one can see the connector arm 19, which is connected at point 18 to the malleable foot 21. The bottom surface 5 is shown having a suction port 11 and a textured area 15. The central open region is shown as 13 but is not particularly noticeable because the figure is shown in two-dimensional instead of three-dimensional. The upper or distal surface 7 is shown being opposite of the bottom surface 5. The tissue surface on which the operation would be carried out is shown as dotted line 22 and is slightly curved. Here the tissue stabilizer has not been placed onto the surface as yet. The malleable foot can be molded to follow the surface to be stabilized and the suction portion which extends in part beyond the foot will then adapt to the surface and will draw the surface into the suction port thus stabilizing the tissue in preparing it for the operation.

The materials that are particularly useful for the tissue stabilizer can be any of those materials that are biologically acceptable to be used by surgeons in operations on tissue, particularly operations on the heart. Thus, the malleable foot can be a metallic material which can be deformed but which will maintain its form once it is deformed. These include stainless steel, aluminum, and precious metals. Alternatively, materials used for the malleable foot can be various plastics which are maleable but which will retain their form once they are molded to the surface configuration as desired. The material covering the malleable foot and comprising the membrane will generally be any polymeric materials, which is suitable for contacting tissue. This can include silicones, polyurethanes, polypropylene, polyethylene, and the like. Sources for the material include those commercially available from sources such as Dow, Bayer, UG and many others. Silicone is preferred, particularly silicone with a durometer rating of about 50–100 Shore.

Turning now to FIG. 4 one sees a view of the bottom of the device in this invention. This is a perspective showing the device 30 generally in a bottom view showing the bottom surface 47 of the lower section device. A suction port 31 is defined by a circular ridge 32 and having a suction opening 33 leading to the suction port and into the internal chamber discussed further in relation to FIG. 5. FIG. 4 is shown with six equivalent suction ports although the number could be greater or lesser, as discussed herein. The suction ports 31 are shown as located around the outer perimeter of the bottom surface of the device away from the central opening 34 and preferably not directly beneath the planar foot. A tapered region 35 preferably surrounds central opening 34. The tapered region fits more closely to the surface of the tissue to be worked on. Although not required there is a slight ridge 36 extending around the perimeter defined area of the bottom. FIG. 4 shows that the surface of the bottom area is stippled or provided with slight bubble-texture on the entire bottom of the surface of the device. This stippling or texturing is a modification that aids in preventing the movement of the device against the tissue on which it is used.

Turning now to FIG. 5 one sees the top view of the internal portion of the bottom section of the device. A suction opening 33 leads to the suction port 31 and a channel 43 leads to the suction opening 33. The channel is defined by ridges 38 above the suction ports. In addition there is a further ridge 39 towards the back of the lower section shown. The ridges 38 and 39 prevent the upper surface which is laminated or molded to the lower section from collapsing on suction opening 33 and preventing a negative pressure from being sustained. Thus when the upper surface is molded to the lower section, a chamber 48 connects each of the suction ports 31 in FIG. 4 and the openings 33 are maintained opened. This advantageous design ensures that the suction opening 33 stays open and does not have the upper surface collapsing on the opening. In forming the chamber 48 a ridge 40 extends around the perimeter of the footprint for receiving the maleable planar foot that is an integral part of the device. The foot, as discussed before may be an integral part of the device and molded with the device or it may be slipped into a sleeve which is formed between the upper and lower sections of the device. The raised rear ridge 42 completes the definition of the internal chamber 48 out of which the air is sucked. The ridge is particularly valuable in the manufacturing process as will be discussed hereinafter.

FIG. 6 is a close-up perspective view of the right-hand side of FIG. 5. Here one can see the ridges 38 above the suction port along with the rear ridge 39 to prevent the upper surface from collapsing into the lumen. Channel 43 is defined by the ridges 38 above the suction port. The rear ridge 42 and internal ridge 40 are shown and further define the chamber.

Turning now to FIG. 7 one sees the end-on view of the device shown in FIG. 4 along lines A–A' in FIG. 6. The circular ridge 32 forms the suction port 31 and the central opening 34 is shown along with the tapered region 35 surrounding the central opening. The outlet port connectable to the reduced pressure area or suction area is shown as 45.

Turning now to FIG. 8, the numerals used are the same as the numerals used to designate the components of FIGS. 4–7. This is a top view of a device 30 of this invention where the top surface 44 is seen. The suction outlet port 45 is provided that allows the internal chamber (not shown) to be evacuated upon connection to a suction pump, syringe, or other means to create a negative pressure. The edge 46 of the bottom section is shown protruding around the top surface 44. The central opening area is shown as 34.

FIG. 9 shows a cross-sectional view of FIG. 8 along line AC—AC, with the top surface 44 and the bottom surface 47 of the lower section of the device 30. In this cross-section view, one also sees the circular ridge 32 in profile which forms the suction port 31 on the bottom surface 47 of the device 30. One also sees the suction outlet port 45 along with the internal ridge 42 as shown in FIG. 5. The planar foot is not shown in this diagram.

FIG. 10 is a cross-section view along lines AD—AD from FIG. 8. This is analogous to the internal perspective view of FIG. 5. Here, the top surface 44 has a region 41 for accepting the planar foot in the device. Suction outlet port 45 extends through the upper surface 44 to the internal chamber 48 defined by the upper surface 44 and the lower section having bottom surface 47. A channel 43 through ridge 38 aids in forming the suction opening 33 for suction port 31.

FIG. 11 is an end view along lines AB—AB in FIG. 8. Here, one can see the bottom surface 47 and the upper surface 44 of device 30. The suction outlet port is shown as 45 with central opening shown as 34. The circular ridge 32 that defines the suction port 31 protrudes from the lower surface 47.

Turning now to FIG. 12, we see the cross-sectional view below the upper surface 44 of FIG. 11 along lines AE—AE. This view of FIG. 12 is comparable to the perspective view of FIG. 5. Here, one can see the open section 34 which exposes the portion of the tissue to be operated upon. A channel 43 runs through the ridges 38 leading to opening 33 and into the suction port 31 on the bottom surface, now shown. The rear ridge 39 assists in preventing the upper surface, not shown, from collapsing to the lower portion of the chamber 48 to reach opening 33 and thus affecting the suction of the device. The chamber 48 is further defined by the ridge 40 running around the perimeter of the device. It can be seen that if the upper surface 44 were placed upon the lower section of the device, a chamber 48 would be formed and the ridges 42, 39, 38 and 40 will all cooperate to keep the upper surface 34 from collapsing and closing chamber 48.

FIG. 13 shows the reverse side of FIG. 12 and is analogous to the perspective drawing shown in FIG. 4. Here one sees the opening 34 of the device 30 and further sees the suction opening 33 leading to the suction port 31 which is defined by circular ridge 32. The lower surface 47 is shown as being stippled across nearly the entire surface, a modification of the surface that helps prevent the movement of the lower surface across the tissue being worked on. The beveled region 35 is shown around the central portion 34 of the device 30.

FIG. 14 is the view along lines AF—AF in FIG. 13 of device 30 without the planar foot and connecting end. The circular ridge 32 which is defining the suction port within the circled ridge. The suction outlet port 45 is shown along with the upper surface 44.

FIG. 15 is analogous to FIG. 4, with like numbers referring to like components. The primary differences are that the device of FIG. 15 has only four total suction ports around the outer perimeter of the bottom surface (as compared to six in FIG. 4) and only portion of the bottom surface is shown as being modified with texturing.

Having described the characteristics of the invention in detail, one can see that an aspect of the invention can be summarized as a tissue stabilizer that comprises a flexible membrane suitable for integration with a malleable planar foot having a central access opening. The membrane comprises a lower section having a bottom surface for contacting the tissue to be stabilized and a top section opposite the lower section. Together the sections form an inner chamber in the membrane. A plurality of suction ports are located on the bottom surface, each suction port being in fluid communication with the chamber through an opening. An outlet port is in fluid communication with the inner chamber and suction ports and can be connected to a negative pressure source. The membrane has a centrally-located open region through which the tissue to be stabilized can be accessed and a sleeve between the top and bottom sections designed to receive the malleable planar foot, which foot has an extension on each side of the central region. When the planar foot is inserted into the sleeve, the membrane and foot may be positioned on a tissue to be stabilized, and a negative pressure is applied to the outlet port. The bottom surface conforms to the surface contour of the tissue to be stabilized through the action of the suction ports and compression by the foot.

Another aspect of the invention can be viewed as a method for stabilizing tissue. The method comprises positioning the tissue stabilizer of this invention on the tissue to be stabilized, then attaching a negative pressure source to the outlet port and providing compressive force to the foot though the rigid arm for a time sufficient to conform the proximal surface of the tissue stabilizer to the tissue area. After the tissue stabilizer has been placed upon the tissue, an operation may be performed on the tissue through the central open region of the foot and membrane. The stabilizer comprises a malleable, planar foot having a central opening, a rigid arm connected to the foot, and a membrane integrated with the foot. The membrane has a shape approximating the foot, a lower section having a bottom surface for contacting the tissue to be stabilized, and a top section opposite the bottom section. An inner chamber in the membrane is in fluid communication with a plurality of suction ports on the bottom surface and with an outlet port for connecting to a negative pressure source. The stabilizer has a centrally-located open region through which the tissue to be stabilized can be accessed and the stabilizer is designed so that when the bottom surface of the membrane is positioned on a tissue to be stabilized and a negative pressure is applied to the outlet port, the bottom surface conforms to the surface contour of the tissue to be stabilized through the action of suction and compression.

Making the Device of the Invention

The device of this invention is made using injection molding techniques. The molds are designed to mold the lower section to the top section in one injection molding process. In a preferred aspect, the process also is designed to make the planar foot an integral part of the device. By reference to FIGS. 1–15, one can understand the process. In general, the steps are as follows: an injection mold is prepared, having the general characteristics that will result in a device shown in FIGS. 1–15. A removable mandrel that provides the internal design for chamber 48 provided in FIG. 5 is placed within the injection molding equipment. A rod defining injection port 45, which rod is removable, is placed within the injection molding apparatus. The desired polymeric material is then injected into the mold with the planar foot in place so that it is integrated into the mold. The polymer is allowed to cure, the rod forming the outlet port is removed and the mandrel defining the inner chamber is removed. Thereafter, an appropriate adhesive is applied to the outer edge of the lower section along the ridge 42 and the edge 49 to adhere the upper section to the lower section of the device and to form a relatively airtight chamber 48 as discussed herein. Once the glue has cured, the device is ready to be used. The adhesive that is particularly valuable for bonding the upper and lower surface at the rear-end is an adhesive for silicon put out by General Electric Corporation of Waterford, New York called RTV adhesive.

In the manufacturing of the device it is preferred that the device is injection molded using an appropriate polymeric material that has a durometer rating that is in the range of about 50–100 Shore, preferably about 60–90 Shore.

In general the width and length of device will be about 1 to 3 inches, preferably about 1½ to 2 inches. The thickness of the membrane will be less than about 0.5 inches, preferably about 0.25 inch, but more than about 0.1 inch. The central opening may vary from about 0.2 to 0.8 inches with a particularly useful opening being about 0.3 to 0.5 inches. Opening 33 may be anywhere from 0.05 inches to 0.1 inch, 0.063 being a particularly useful diameter of that opening. The internal diameter of the suction port 31 formed by circular ridge 32 may be from 0.1 to 0.3, with 0.02 inches particularly valuable. The centers of each suction port 31 may be anywhere from 0.3 to 0.5 inches, with 0.345 being useful for a device having 3 ports and 0.4 being useful for a device having only 2 ports per side.

The invention now being fully described, it will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

The subject matter claimed is:

1. A tissue stabilizer that comprises
   a malleable planar foot having an open central region;
   a rigid arm connected to the foot;
   a membrane integrated with the foot and having a shape approximating the foot, a lower section having a bottom surface for contacting the tissue to be stabilized, and an upper section opposite the lower section;
   an inner chamber in the membrane;
   a plurality of suction ports on the bottom surface, the suction ports in fluid communication with the inner chamber through an opening;
   an outlet port connecting the inner chamber and suction ports to a negative pressure source; and
   a centrally-located open region through which the tissue to be stabilized can be accessed,
   the stabilizer being designed so that when the bottom surface of the membrane is positioned on a tissue to be stabilized and a negative pressure is applied to the outlet port, the bottom surface tends to conform to the surface contour of the tissue to be stabilized through the action of suction by the ports and compression by the foot.

2. The tissue stabilizer of claim 1, wherein the suction ports are located around the outer perimeter of the bottom surface not directly beneath the malleable planar foot.

3. The tissue stabilizer of claim 1, wherein at least a portion of the bottom surface is modified to reduce movement of the stabilizer relative to the tissue to be stabilized.

4. The tissue stabilizer of claim 3, wherein the bottom surface around the central opening is textured.

5. The tissue stabilizer of claim 3, wherein nearly all of the bottom surface is textured.

6. The tissue stabilizer of claim 3, wherein the modified bottom surface has a biocompatable medical-grade adhesive on it.

7. The tissue stabilizer of claim 1, wherein the shape of the foot and bladder is a "U" shape.

8. The tissue stabilizer of claim 1, wherein the shape of the foot and bladder is adjusted to approximate the contours of the surface of the tissue to be stabilized.

9. The tissue stabilizer of claim 1, wherein the tissue is of an internal organ.

10. The tissue stabilizer of claim 1, wherein the membrane is made of a medical grade, flexible polymeric material.

11. The tissue stabilizer of claim 10, wherein the membrane is a silicon polymer having a durometer rating of 50 to 100 Shore.

12. The tissue stabilizer of claim 1, wherein the distance between the bottom surface and the top surface of the membrane is about 0.1 inch to about 0.5 inch, the width of the tissue stabilizer is about 1.0 inch to about 3.0 inches, and the length of the tissue stabilizer is about 1.0 inch to about 3.0 inches.

13. The tissue stabilizer of claim 11, wherein the volume of the internal chamber within the membrane is about 1500 $mm^3$ to about 24,000 $mm^3$.

14. The tissue stabilizer of claim 1, wherein the surface area of the bottom surface is about 1.0 inch to about 9.0 inches.

15. The tissue stabilizer of claim 1, in combination with a negative pressure source.

16. The tissue stabilizer of claim 1, wherein the inner chamber has a series of ridges protecting the opening leading to the suction port to prevent the upper section from covering the opening and preventing the suction action during operation.

17. A membrane for aiding the stabilization of a tissue during an operation on such tissue, which membrane comprises
- a lower section having a bottom surface for contacting the tissue to be stabilized;
- a top section opposite the lower section;
- at least one inner chamber in the membrane;
- a plurality of suction ports on the bottom surface, each suction port being in fluid communication with the chamber through an opening;
- an outlet port connecting the inner chamber and suction ports to a negative pressure source;
- a centrally-located open region through which the tissue to be stabilized can be accessed; and
- a sleeve between the top and bottom sections designed to receive a malleable planar foot having an extension on each side of the central region,
- the membrane being designed so that when the planar foot is inserted into the sleeve, the membrane and foot are positioned on a tissue to be stabilized, and a negative pressure is applied to the port, the bottom surface conforms to the surface contour of the tissue to be stabilized through the action of suction by the ports and compression by the foot.

18. The membrane of claim 17, wherein the plurality of suction ports are located around the outer perimeter of the bottom surface away from the sleeve into which the planar foot fits.

19. The membrane of claim 17, wherein at least a portion of the bottom surface is modified to reduce movement of the bladder relative to the tissue to be stabilized.

20. The membrane of claim 19, wherein nearly all of the bottom surface is textured.

21. The membrane of claim 19, wherein the modified bottom surface has a biocompatable medical grade adhesive on it.

22. The membrane of claim 17, wherein the sleeve is designed to receive a "U" shaped foot with an extension of the "U" on each side of the central opening.

23. The membrane of claim 17, wherein after the foot is inserted into the membrane, the shape of the bottom surface is adjusted to fit the contours of the surface of the tissue to be stabilized.

24. The membrane of claim 17, wherein the tissue is chosen from tissue of an internal organ.

25. The membrane of claim 17, made of a medical grade, flexible polymeric material.

26. The membrane of claim 24 made of a silicone polymer having a durometer rating of about 50 to 100 Shore.

27. The membrane of claim 17, wherein the distance between the bottom surface and the top surface of the bladder is about 0.1 inch to about 0.5 inch, the width of the tissue stabilizer is about 1.0 inch to about 3.0 inches, and the length of the tissue stabilizer is about 1.0 inch to about 3.0 inches.

28. The membrane of claim 17, wherein the volume of the chamber is about 1500 $mm^3$ to about 24,000 $mm^3$.

29. The membrane of claim 17, wherein the surface area of the bottom surface is about 1.0 square inch to about 9.0 square inches.

30. The membrane of claim 17, in combination with a negative pressure source and an inserted planar foot.

31. The membrane of claim 17, wherein the inner chamber has a series of ridges protecting the opening leading to the suction port to prevent the upper section from covering the opening and preventing the suction action during operation.

32. A method for stabilizing tissue, which method comprises
- (a) positioning a tissue stabilizer on the tissue to be stabilized, wherein the tissue stabilizer comprises (i) a malleable, planar foot having a central opening; (ii) a rigid arm connected to the foot; (iii) a membrane integrated with the foot and having a shape approximating the foot, a lower section having a bottom surface for contacting the tissue to be stabilized, and a top section opposite the bottom section; (iv) at least one inner chamber in the membrane; (v) a plurality of suction ports on the bottom surface, each suction port being in fluid communication with the inner chamber; (vi) an outlet port for connecting the inner chamber and suction ports to a negative pressure source; (vii) a centrally-located open region through which the tissue to be stabilized can be accessed; and (viii) the stabilizer being designed so that when the bottom surface of the membrane is positioned on a tissue to be stabilized and a negative pressure is applied to the outlet port, the bottom surface conforms to the surface contour of the tissue to be stabilized through the action of suction and compression and
- (b) attaching a negative pressure source to the outlet port and providing compressive force to the foot though the rigid arm for a time sufficient to conform the proximal surface of the tissue stabilizer to the tissue area.

33. The method of claim 32, wherein the tissue is of an internal organ.

34. The method of claim 33, wherein the tissue to be stabilized is heart tissue.

35. The method of claim 32, wherein after the tissue stabilizer has been placed upon the tissue, an operation is performed on the tissue through the centrally-located open region of the foot and membrane.

36. The method of claim 32, wherein the shape of the foot and membrane is a "U" shape.

37. The method of claim 32, wherein the suction ports are located around the outer perimeter of the bottom surface not beneath the malleable planar foot.

38. The method of claim 32, wherein at least a portion of the bottom surface around the central opening is modified to reduce the movement of the stabilizer relative to the tissue to be stabilized.

39. The method of claim 38, wherein the modified area of the bottom surface is coated with a light medical adhesive to allow it to lightly adhere to the tissue surface.

40. The method of claim 38, wherein the modified area of the bottom surface is textured.

41. The method of claim 38, wherein nearly the entire bottom surface is textured.

42. A process for making the tissue stabilizer of claim 1 using an injection molding technique, which process comprises
- preparing an appropriate mold provided with removable mandrels for the inner chamber and the outlet port of the membrane,
- position the foot and connecting rod with the mold to be integrated into the membrane,
- injecting a polymeric material into the mold,
- curing the polymer,
- removing the mandrels, and
- adhering the upper section and lower section to form the chamber.

* * * * *